(12) United States Patent
Orchansky et al.

(10) Patent No.: US 7,645,749 B2
(45) Date of Patent: Jan. 12, 2010

(54) STEROL/STANOL NITRODERIVATIVES AND USE THEREOF

(75) Inventors: Patricia Liliana Orchansky, Vancouver (CA); James P. Kutney, Vancouver (CA)

(73) Assignee: Forbes Medi-Tech Inc., Vancouver, British Columbia (CA)

( * ) Notice: Subject to any disclaimer, the term of this patent is extended or adjusted under 35 U.S.C. 154(b) by 340 days.

(21) Appl. No.: 11/396,924

(22) Filed: Apr. 3, 2006

(65) Prior Publication Data

US 2007/0232580 A1 Oct. 4, 2007

(51) Int. Cl.
*A61K 31/585* (2006.01)
*A61K 31/56* (2006.01)
*C07J 9/00* (2006.01)

(52) U.S. Cl. .................. 514/175; 514/182; 552/544
(58) Field of Classification Search ................ 552/544; 514/175, 182
See application file for complete search history.

(56) References Cited

FOREIGN PATENT DOCUMENTS

| CA | 2370446 | 10/2000 |
|----|---------|---------|
| CA | 2518506 | 11/2004 |

*Primary Examiner*—Barbara P Badio
(74) *Attorney, Agent, or Firm*—Kirton & McConkie; Evan R. Witt

(57) ABSTRACT

Sterol and stanol nitro derivatives and their use in treating or preventing cardiovascular disease, its underlying conditions and other disorders are disclosed. The disclosed nitro derivatives are synthesized by ester linkage of a nitric oxide (NO)-releasing moiety to a sterol or stanol compound.

10 Claims, No Drawings

STEROL/STANOL NITRODERIVATIVES AND USE THEREOF

FIELD OF THE INVENTION

This present invention relates to the field of sterol and stanol derivatives, pharmaceutical compositions comprising these derivatives and various uses of these derivatives in a wide variety of therapeutic areas.

BACKGROUND OF THE INVENTION

While recent advances in science and technology are helping to improve quality and add years to human life, the prevention of atherosclerosis, the underlying cause of cardiovascular disease ("CVD") has not been sufficiently addressed. Atherosclerosis is a degenerative process resulting from interplays of inherited (genetic) factors and environmental factors such as diet and lifestyle. Research to date suggest that cholesterol may play a role in atherosclerosis by forming atherosclerotic plaques in blood vessels, ultimately cutting off blood supply to the heart muscle or alternatively to the brain or limbs, depending on the location of the plaque in the arterial tree (1,2). Overviews have indicated that a 1% reduction in a person's total serum cholesterol yields a 2% reduction in risk of a coronary artery event (3). Statistically, a 10% decrease in average serum cholesterol (e.g. from 6.0 mmol/L to 5.3 mmol/L) may result in the prevention of 100,000 deaths in the United States annually (4).

Sterols are naturally occurring compounds that perform many critical cellular functions. Phytosterols such as campesterol, stigmasterol and beta-sitosterol in plants, ergosterol in fungi and cholesterol in animals are each primary components of cellular and sub-cellular membranes in their respective cell types. The dietary source of phytosterols in humans comes from plant materials i.e. vegetables and plant oils. The estimated daily phytosterol content in the conventional western-type diet is approximately 60-80 milligrams in contrast to a vegetarian diet which would provide about 500 milligrams per day.

Phytosterols have received a great deal of attention (particularly over the past ten years) due to their ability to decrease serum cholesterol levels when fed to a number of mammalian species, including humans. While the precise mechanism of action remains largely unknown, the relationship between cholesterol and phytosterols is apparently due in part to the similarities between the respective chemical structures (the differences occurring in the side chains of the molecules). It is assumed that phytosterols displace cholesterol from the micellar phase and thereby reduce its absorption or possibly compete with receptor and/or carrier sites in the cholesterol absorption process.

This history of phytosterols and use in cholesterol lowering goes back much further than this past decade of resurgence. Over forty years ago, Eli Lilly marketed a sterol preparation from tall oil and later from soybean oil called Cytellin™ which was found to lower serum cholesterol by about 9% according to one report (5). Various subsequent researchers have explored the effects of sitosterol preparations on plasma lipid and lipoprotein concentrations (6) and the effects of sitosterol and campesterol from soybean and tall oil sources on serum cholesterols (7). A composition of phytosterols which has been found to be highly effective in lowering serum cholesterol is disclosed in U.S. Pat. No. 5,770,749 to Kutney et al. and comprises no more than 70% by weight beta-sitosterol, at least 10% by weight campesterol and stigmastanol (beta-sitostanol). It is noted in this patent that there is some form of synergy between the constituent phytosterols, affording even better cholesterol-lowering results than had been previously achieved.

Despite the obvious and now well recorded advantages of phytosterols, not only in the treatment of CVD and its underlying conditions such as hypercholesterolemia, hyperlipidemia, atherosclerosis, hypertension, thrombosis but in the treatment of other diseases such as Type II diabetes, dementia cancer and aging, the administration of phytosterols and the incorporation thereof into foods, pharmaceuticals and other delivery vehicles was complicated by the fact that they are highly hydrophobic (i.e. they have poor water solubility). This problem was finally addressed by the creation of ascorbic acid derivatives of phytosterols and phytostanols, as described in WO 01/00653, such derivatives being highly water soluble and capable of being readily incorporated into various pharmaceutical delivery matrices. Compounds within this ascorbyl derivative family have been developed by Forbes Medi-Tech Inc. under the reference name VP4.

Phytosterols and phytostanols remain compounds of great interest in the cardiovascular therapeutics field. It is an object of the present invention to enhance the therapeutic efficacy of phytosterols and phytostanols in manners heretofore unconsidered.

SUMMARY OF THE INVENTION

The present invention provides novel phytosterol and phytostanol nitroderivatives, including pharmaceutically acceptable salts or stereoisomers thereof, represented by the general formulae:

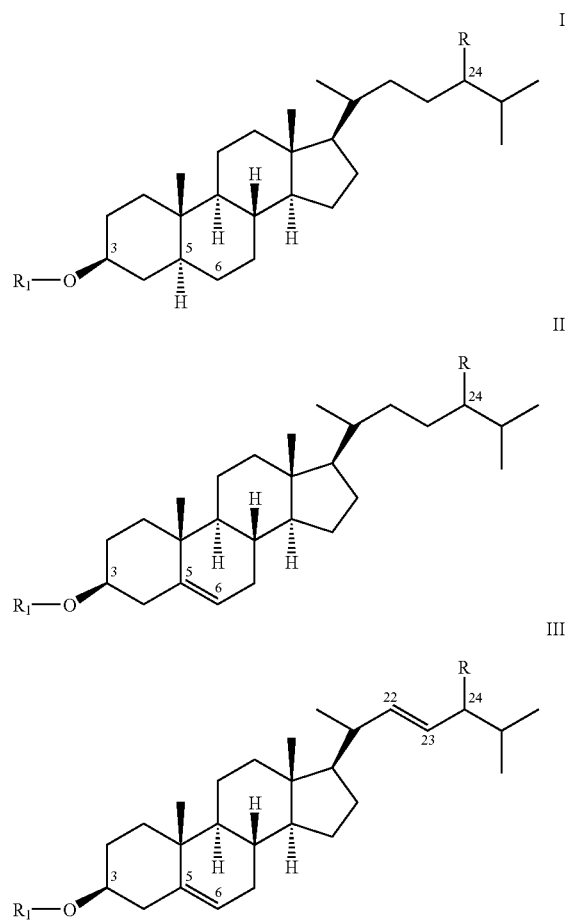

wherein in the foregoing formulae, R is selected from CH₃ and CH₂CH₃ and R₁ is an aromatic or aliphatic NO releasing agent selected from the group consisting of:

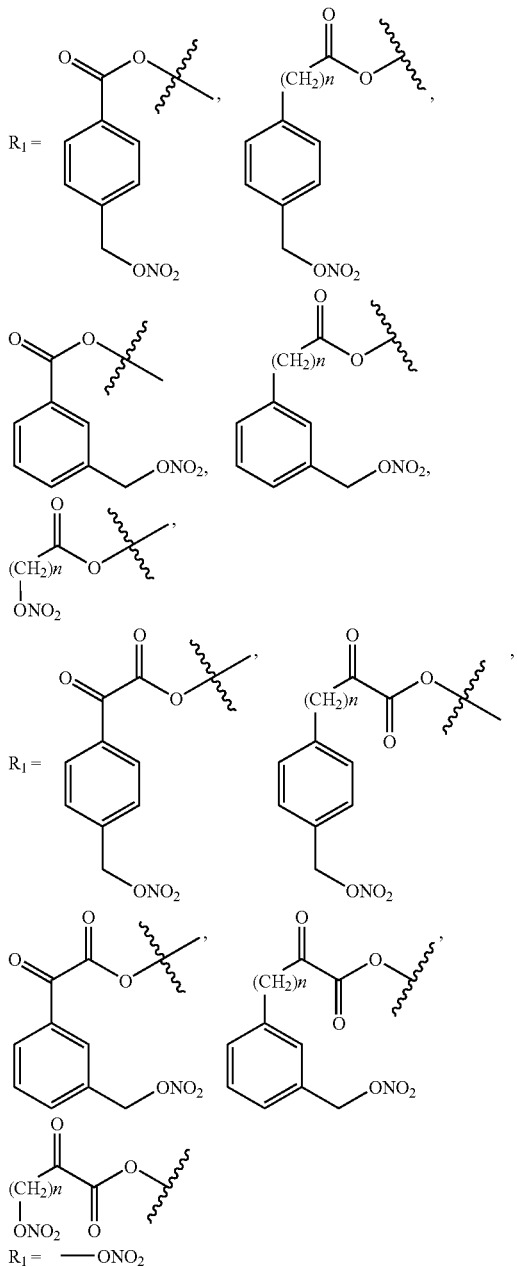

wherein n is an integer from 1 to 20.

The present invention further comprises pharmaceutical compositions for treating or preventing CVD and its underlying conditions including atherosclerosis, hypercholesterolemia, hyperlipidemia, hypertension, thrombosis, and related diseases such as Type II diabetes, as well as other diseases that include oxidative damage as part of the underlying disease process such as dementia, Alzheimer's disease, aging, and cancer which comprises one or more derivatives as described in formulae I through III with the above noted formulae, and a pharmaceutically acceptable carrier therefore.

The present invention further provides a method for treating or preventing CVD and its underlying conditions including atherosclerosis, hypercholesterolemia, hyperlipidemia, hypertension, thrombosis, and related diseases such as Type II diabetes, as well as other diseases that include oxidative damage as part of the underlying disease process such as dementia, aging, and cancer by administering to an animal one or more derivatives as described in formulae I through III and a pharmaceutically acceptable carrier therefore.

The phytosterol and phytostanol nitroderivatives of the present invention represent an unexpected advantage over the known phytosterols, in free or derivatized form. Contrary to any expectation, the derivatives of the present invention are characterized by the fact that they show an improved therapeutic profile and high activity across a variety of therapeutic areas.

The derivatives of the present invention can be prepared and used as such or they can be easily incorporated into a wide selection of pharmaceutical preparations.

PREFERRED EMBODIMENTS OF THE INVENTION

The following detailed description is provided to aid those skilled in the art in practising the invention. However this detailed description should not be construed so as to unduly limit the scope of the present invention. Modifications and variations to the embodiments discussed herein may be made by those with ordinary skill in the art without departing from the spirit or scope of the present invention.

According to the present invention, there are provided novel nitroderivatives synthesized by ester linkage of an NO-releasing moiety to a sterol or stanol compound. These derivatives are suitable for use per se in treating or preventing CVD and its underlying conditions, such as atherosclerosis, hypercholesterolemia, hyperlipidemia, hypertension, thrombosis, and related diseases such as Type II diabetes, as well as in treating and preventing other diseases that include oxidative damage as part of the underlying disease process such as dementia, Alzheimer's disease, aging, and cancer.

It should be noted that, throughout this disclosure, the terms "derivative", "structure" and "analogue" are used interchangeably to describe the novel unitary compounds which are covered by formulae I through III as provided herein.

As used herein, "NO" refers to nitric oxide. Nitric oxide (NO) is a highly reactive, diffusible, and unstable radical which is a unique messenger molecule involved in the regulation of diverse physiological processes including smooth muscle contractility, platelet reactivity and central and peripheral neurotransmission. In the immune system NO has been recognized as an important effector molecule for macrophages as well as a homeostatic regulator. Depending on the type and phase of the inflammatory reaction and the individual vascular or cellular responses studied, NO can exert both proinflammatory and antiinflammatory actions.

Unlike most other neurotransmitters that only transmit information from a presynaptic to a postsynaptic neuron, the small NO molecule can diffuse all over and can thereby act on several nearby neurons, even on those not connected by a synapse. It is conjectured that this process may be involved in memory through the maintenance of long-term potentiation. In addition, NO is an important non-adrenergic, non-cholinergic (NANC) neurotransmitter in various parts of the gastrointestinal tract. It causes relaxation of the gastrointestinal smooth muscle. In the stomach it increases the capacity of the fundus to store food/fluids.

The endothelium (inner lining) of blood vessels use NO to signal the surrounding smooth muscle to relax, thus dilating the artery and increasing blood flow. This underlies the action of nitroglycerin, amyl nitrate and other nitrate derivatives in the treatment of heart disease: The compounds are converted to NO (by a process that is not completely understood), which in turn dilates the coronary artery (blood vessels around the heart), thereby increasing its blood supply.

The term "NO releasing agent" refers to all aliphatic and aromatic NO releasing compounds described herein.

As used herein, the term "sterol" includes all sterols without limitation, for example: (from any source and in any form: α, β and γ) sitosterol, campesterol, stigmasterol, brassicasterol (including dihydrobrassicasterol), desmosterol, chalinosterol, poriferasterol, clionasterol, ergosterol, coprosterol, codisterol, isofucosterol, fucosterol, clerosterol, nervisterol, lathosterol, stellasterol, spinasterol, chondrillasterol, pepostanol, avenasterol, isoavenasterol, fecosterol, pollinastasterol, cholesterol and all natural or synthesized forms and derivatives thereof, including isomers.

The term "stanol" refers to, for example: (from any source and in any form: α, β and γ) saturated or hydrogenated sterols including all natural or synthesized forms and derivatives thereof, and isomers, including sitostanol, campestanol, stigmastanol, brassicastanol (including dihydrobrassicastanol), desmostanol, chalinostanol, poriferastanol, clionastanol, ergostanol, coprostanol, codistanol, isofucostanol, fucostanol, clerostanol, nervistanol, lathostanol, stellastanol, spinastanol, chondrillastanol, pepostanol, avenastanol, isoavenastanol, fecostanol, and pollinastastanol.

It is to be understood that modifications to the sterols and stanols i.e. to include side chains also falls within the purview of this invention. It is also to be understood that, when in doubt throughout the specification, and unless otherwise specified, the term "sterol" encompasses both sterol and stanol. The terms "phytosterol" and "phytostanol" may also be used and refer to all plant-derived sterols or stanols respectively.

The sterols and stanols for use in forming derivatives in accordance with this invention may be procured from a variety of natural sources or they may be artificially synthesized. For example, they may be obtained from the processing of plant oils (including aquatic plants) such as corn oil and other vegetable oils, wheat germ oil, soy extract, rice extract, rice bran, rapeseed oil, sunflower oil, sesame oil and fish (and other marine-source) oils. They may also be derived from yeasts and fungi, for example ergosterol. Accordingly, the present invention is not to be limited to any one source of sterols. U.S. Pat. No. 4,420,427 teaches the preparation of sterols from vegetable oil sludge using solvents such as methanol. Alternatively, phytosterols and phytostanols may be obtained from tall oil pitch or soap, by-products of forestry practises as described in U.S. Pat. No. 5,770,749, incorporated herein by reference. A further method of extracting sterols and stanols from tall oil pitch is described in Canadian Patent Application Serial No. 2,230,373 which was filed on Feb. 20, 1998 (corresponding to PCT/CA99/00150 which was filed on Feb. 19, 1999) and U.S. patent application Ser. No. 10/060,022 which was filed on Jan. 28, 2002 the contents of all of which are incorporated herein by reference.

Accordingly, it is to be understood that the widest possible definition is to be accorded to the terms "sterol" and "stanol" as used herein, including, but not limited to: free sterols and stanols, esterified sterols and stanols with aliphatic or aromatic acids (thereby forming aliphatic or aromatic esters, respectively), phenolic acid esters, cinnamate esters, ferulate esters, phytosterol and phytostanol glycosides and acylated glycosides or acylglycosides. Thus, the terms "sterols" and "stanols" encompasses all analogues, which may further have a double bond at the 5-position in the cyclic unit as in most natural sterols, or one or more double bonds at other positions in the rings (for example, 6, 7, 8(9), 8(14), 14 5/7) or no double bonds in the cyclic unit as in stanols. Further, there may be additional methyl groups as, for example, in $\alpha_1$-sitosterol.

Sterols and/or stanols once isolated from their source are generally formed into a solid powder through precipitation, filtration and drying, spray drying, lyophilization or by other conventional work-up techniques.

In one preferred form, the nitroderivative of the present invention is formed of naturally-derived or synthesized beta-sitosterol, campestanol, sitostanol and campesterol. The most preferred form of nitroderivative of the present invention is one or more of the following: sitosteryl nitroesters or nitrates; sitostanyl nitroesters or nitrates, campesteryl nitroesters or nitrates; campestanyl nitroesters or nitrates and sterodienyl nitroesters or nitrates (brassicasteryl, stigmasteryl).

Within the scope of the present invention, an NO releasing agent is linked directly to sterol and/or stanol based compounds.

The reaction by which this may be achieved is simple and utilizes the fact that carboxylic acids (of which all but one of the NO releasing agents within the scope of the present invention are) react with alcohols (OH groups are inherent on the sterols/stanols) in the presence of an acid catalyst to produce esters. Once such reaction is called "Fischer esterification", and is well known and practised in the art. It is to be understood that while the example below shows the NO releasing agent as an aromatic compound, the process is equally applicable to the selected aliphatic NO releasing agents described herein.

If $R_1$ is —$ONO_2$, then the process of preparing the compound will be somewhat different i.e. not a classic esterification. For example, one way to prepare the nitrates, wherein the NO releasing agent is not a carboxylic acid (—$ONO_2$), is via the transformation of the alcohol (the sterol/stanol moiety [Z]) to an alkylhalide as follows:

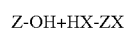

wherein X=halide such as bromine, chlorine, fluorine.

Subsequently, the —$ONO_2$ may be substituted under appropriate reaction conditions which are known and applied in the art.

The compounds of the present invention, which have one or more asymmetric carbon atoms, can exist as optically pure enantiomers, pure diastereomers, enantiomers mixtures, diastereomers mixtures, enantiomers racemic mixtures, racemates or racemates mixtures. Within the scope of the present invention are all possible isomers, stereoisomers and their mixtures of the compounds having structures I through XVI.

Salts

The present invention encompasses not only the parent structures, the nitrosated sterol/stanol esters, but also the salts thereof. These salts are even more water soluble than the corresponding parent compounds and therefore their efficacy in vivo is enhanced. It is possible to form such salts in the particular compounds possessing a free "—OH".

In such cases, salt formation of the derivatives of the present invention can be readily performed by treatment of the parent compound with a series of bases (for example, sodium methoxide or other metal alkoxides) to produce the corresponding alkali metal salts. Other metal salts of calcium, magnesium, manganese, copper, zinc, and the like can be generated by reacting the parent with suitable metal alkoxides. Thus hydrogen presents the parent compound and any metal, alkali earth metal, or alkali metal represents the corresponding salt.

Combination of Derivatives with HMG-Coenzyme A Reductase Inhibitors

In a further embodiment, the derivatives of the present invention may be combined, prior to administration or concurrently, with one or more agents or compounds which treat cardiovascular disease. For example, they may be combined with compounds that inhibit cholesterol synthesis. These compounds include, but are not limited to 3-hydroxy-3-methyl glutaryl coenzyme-A (HMG-CoA) reductase inhibitors and nitrosated 3-hydroxy-3-methyl glutaryl coenzyme-A (HMG-CoA) reductase inhibitors. The combination of these cholesterol synthesis-limiting compounds and the phytosterol derivatives of the present invention is synergistic and initiates and perpetuates both "systemic or enteric" and "extrinsic" effects.

Although the mechanism of action of the derivatives of the present invention is not certain, it is believed that cholesterol levels are lowered through a process called "biliary diversion", the uncoupling of communication between the biliary enterocytes and the hepatocytes. Enteric cholesterol production may increase but cholesterol is released in the bile and not reabsorbed through the enterocytes. Any cholesterol synthesis limiting compound would work in concert with these derivatives as the mechanism of the mechanism of the former is the decrease of enteric cholesterol synthesis and bile cholesterol secretion. As cholesterol synthesis is decreased, the phytosterol/cholesterol intestinal ratio increases which decreases cholesterol absorption and increases phytosterol transport via the enterocyte shuttle mechanism.

The finding of this synergistic co-effect between the phytosterol derivatives of the present invention and the compounds which limit cholesterol synthesis, such as statins, is critically important as the dosage of these latter compounds may be significantly reduced when administered in conjunction with the derivatives described herein. It has recently been discovered that there are some critical side-effects to statins such as Lovastatin, so the dosage reduction afforded by the synergy with the derivatives described herein is particularly compelling. Examples of other statins with which the derivative of the present invention may be combined include: atorvastatin (Lipitor™), superstatin, simvastatin (Zocor™), pravastatin (Pravachol™) and rosuvastatin (Crestor™).

In the alternative, the compounds of the present invention may be combined, prior to administration or concurrently, with one or more compounds selected from the group consisting of: ACE inhibitors, angiotensin II receptor antagonists, beta-andrenergic blockers, calcium channel blockers, anti-thrombotics such as aspririn, nitrosated ACE inhibitors, nitrosated angiotensin II receptor antagonists, nitrosated beta-andrenergic blockers and nitrosated aspirin.

Thus, the present invention further comprises pharmaceutical kits comprising one or more containers filled with one or more of the compounds and/or compositions of the present invention and one or more "other" compounds used to treat cardiovascular disease, such as statins, as noted above.

Potential Advantages of Novel Phytosterol Analogues

The novel derivatives of the present invention, containing at least one NO releasing atom/agent, and a sterol/stanol moiety affords many therapeutic advantages. The compounds of formulae I through III are prodrugs for sterols/stanols and NO. Under physiological conditions, NO will be released from the sterol "carrier" molecule revealing broader and more pronounced pharmacological activity that either NO or sterols alone.

Methods of Use

The sterol/stanol nitroderivatives of the present invention may be administered to animals, in particular humans, directly and without further modification or may be treated to enhance further the solubility and/or dispersability. Alternatively, the derivatives may be incorporated into various vehicles as described further below in order to treat and/or prevent CVD, its underlying conditions such as hypercholesterolemia, hyperlipidemia, arteriosclerosis, hypertension, thrombosis, related diseases such as Type II diabetes, as well as other diseases that include oxidative damage as part of the underlying disease process such as dementia, aging, and cancer. In populations, which are considered "high-risk" for CVD or any of the oxidation related disorders, it is contemplated that the derivatives of the present invention be used in primary, secondary and tertiary treatment programs.

Without limiting the generality of the foregoing, the derivatives of the present invention may be admixed with various carriers, excipients or adjuvants to assist in direct administration or to assist in the incorporation of the composition into pharmaceuticals. In order to appreciate the various possible vehicles of the delivery of the derivatives, the list below is provided. The doses of the derivatives will vary depending upon, among other factors, the mode of delivery, the patient size and condition, the result to be achieved, as well as other factors known to those skilled in the art of medicinal agents.

Pharmaceutical Dosage Forms:

It is contemplated within the scope of the present invention that the derivatives of the present invention may be incorporated into various conventional pharmaceutical preparations and dosage forms such as tablets (plain and coated) for use orally, bucally or lingually, capsules (hard and soft, gelatin, with or without additional coatings) powders, granules (including effervescent granules), pellets, microparticulates, solutions (such as micellar, syrups, elixirs and drops), lozenges, pastilles, ampoules, emulsions, microemulsions, ointments, creams, suppositories, slurries, gels, transdermal patches and modified release dosage forms together with customary excipients and/or diluents and stabilizers.

The compounds of the present invention can be administered to a patient either by themselves, or in pharmaceutical compositions where they are mixed with suitable carriers, adjuvants or excipients.

Use of pharmaceutically acceptable carriers to formulate the compounds herein disclosed for the practice of the invention into dosages suitable for systemic administration is within the scope of the invention. With proper choice of carrier and suitable manufacturing practice, the compounds of the present invention, in particular, those formulated as solutions, may be administered parenterally, such as by intravenous injection.

Pharmaceutical compositions, comprising one or more of the compounds of the present invention, include compositions wherein the active ingredients are contained in an effective amount to achieve their intended purpose. Determination of the effective amounts within such compositions is well within the capability of those skilled in the art, especially in light of the disclosure provided herein.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

It is contemplated within the scope of the present invention that the compositions of the present invention may be incorporated into various conventional pharmaceutical preparations and dosage forms such as tablets (plain and coated) for use orally, bucally or lingually, capsules (hard and soft, gelatin, with or without additional coatings) powders, granules (including effervescent granules), pellets, microparticulates, solutions (such as micellar, syrups, elixirs and drops), lozenges, pastilles, ampoules, emulsions, microemulsions, ointments, creams, suppositories, gels, transdermal patches and modified release dosage forms together with customary excipients and/or diluents and stabilizers.

The compositions of the present invention, adapted into the appropriate dosage form as described above may be administered to animals, including humans, orally, by injection (intravenously, subcutaneously, intra-peritoneally, intra-dermally or intra-muscularly), topically or in other ways.

Preferably, the compositions of the present invention are delivered in the form of phospholipid systems such as liposomes and other hydrated lipid phases, by physical inclusion. This inclusion refers to the entrapment of molecules without forming a covalent bond and is widely used to improve the solubility and subsequent dissolution of active ingredients.

Hydrated lipid systems, including liposomes, can be prepared using a variety of lipid and lipid mixtures, including phospholipids such as phosphatidylcholine (lecithin), phosphodiglyceride and sphingolipids, glycolipids, and the like. The lipids may preferably be used in combination with a charge bearing substances such as charge-bearing phospholipids, fatty acids, and potassium and sodium salts thereof in order to stabilize the resultant lipid systems. A typical process of forming liposomes is as follows:

1) dispersion of lipid or lipids and the composition of the present invention in an organic solvent (such as chloroform, dichloromethane, ether, ethanol or other alcohol, or a combination thereof). A charged species may be added to reduce subsequent aggregation during liposome formation. Antioxidants (such as ascorbyl palmitate, alpha-tocopherol, butylated hydroxytoluene and butylated hydroxyanisole) may also be added to protect any unsaturated lipids, if present;
2) filtration of the mixture to remove minor insoluble components;
3) removal of solvents under conditions (pressure, temperature) to ensure no phase separation of the components occur;
4) hydration of the "dry" lipid mixture by exposure to an aqueous medium containing dissolved solutes, including buffer salts, chelating agents, cryoprotectorants and the like; and
5) reduction of liposome particle size and modification of the state of lamellarity by means of suitable techniques such as homogenization, extrusion etc.

Any procedure for generating and loading hydrated lipid with active ingredients, known to those skilled in the art, may be employed within the scope of this invention. Variations on these processes are described in U.S. Pat. No. 5,096,629 which is also incorporated herein by reference.

U.S. Pat. No. 4,508,703 (also incorporated herein by reference) describes a method of preparing liposomes by dissolving the amphiphillic lipidic constituent and the hydrophobic constituent to form a solution and thereafter atomizing the solution in a flow of gas to produce a pulverent mixture.

In another preferred form, the compositions of the present invention can be administered as cyclodextrin complexes. Cyclodextrins are a class of cyclic oligosaccharide molecules comprising glucopyranose sub-units and having a toroidal cylindrical spatial configuration. Commonly available members of this group comprise molecules containing six (alpha-cyclodextrin), seven (beta-cyclodextrin) and eight (gamma-cylcodextrin) glucopyranose molcules, with the polar (hydrophilic) hydroxyl groups oriented to the outside of the structure and the apolar (lipophilic) skeletal carbons and ethereal oxygens lining the interior cavity of the toroid. This cavity is capable of accommodating (hosting) the lipophilic moiety of an active ingredient (the guest molecule, here the composition of the present invention) by bonding in a non-covalent manner to form an inclusion complex.

The external hydroxyl substituents of the cyclodextrin molecule may be modified to form derivatives having improved solubility in aqueous media along with other desired enhancements, such as lowered toxicity, etc. Examples of such derivatives are: alkylated derivatives such as 2,6-dimethyl-beta-cyclodextrin; hydroxyalkylated derivatives such as hydroxypropyl-beta-cyclodextrin; branched derivatives such as diglucosly-beta-cyclodextrin; sulfoalkyl derivatives such as sulfobutylether-beta-cyclodextrin; and carboxymethylated derivatives such as carboxymethyl-beta-cylcodextrin. Other types of chemical modifications, known to those in the art, are also included within the scope of this invention.

The cyclodextrin complex often confers properties of improved solubility, dispersability, stability (chemical, physical and microbiological), bioavailability and decreased toxicity on the guest molecule.

There are a number of ways known in the art to produce a cyclodextrin complex. Complexes may be produced, for example, by using the following basic methods: stirring the anthocyanin composition into an aqueous or mixed aqueous-organic solution of the cyclodextrin, with or without heating; kneading, slurrying or mixing the cyclodextrin and the present composition in a suitable device with the addition of an appropriate quantity of aqueous, organic or mixed aqueous-organic liquid, with or without heating; or by physical admixture the cylcodextrin and the composition of the present invention using a suitable mixing device. Isolation of the inclusion complex so formed may be achieved by co-precipitation, filtration and drying; extrusion/spheronisation and drying; subdivision of the moist mass and drying; spray drying; lyophilization or by other suitable techniques depending on the process used to form the cyclodextrin complex. A further optional step of mechanically grinding the isolated solid complex may be employed.

These cyclodextrin complexes further enhance the solubility and dissolution rate and increase the stability of the present compositions.

The precise modes of delivery of the composition of the present invention in each case will depend upon the objectives of the administration protocol i.e. whether it be preventing, reducing, eliminating or ameliorating a dyslipidemic condition or disorder. In the case of existing conditions and disorders, it will depend upon the severity of the disorder, and as discussed above, the age, size and gender of the individual. Determining appropriate dosages and administration schedules is well within the purview of one skilled in this field.

EXAMPLES

The present invention is described by the following examples which are provided for illustrative purposes and are not intended, in any way, to limit the scope of the present invention:

Example 1

Synthesis of 4-(nitromethyl)benzoic Acid—One Example of a NO Releasing Reagent

The commercially available 4-(hydroxymethyl)benzoic acid (10 g) was reacted with 3 equivalents of silver nitrate in acetonitrile as solvent. The reaction was allowed to proceed at room temperature for several hours and the resulting 4-(nitromethyl)benzoic acid precipitated from the reaction mixture upon addition of water. The product (8 g) obtained as a white powder, after drying, was utilized in the reaction below, without further purification.

Example 2

Synthesis of Phytostanyl-4-nitromethyl Benzoic Acid Ester

The phytostanol mixture (beta-sitostanol:campestanol in approximate ratio of 2:1; 5 g) was reacted with 4 equivalents of 1,3-dicyclohexyl carbodiimide (DCC) in methylene chloride and 4 equivalents of 4-(nitromethyl)benzoic acid, The mixture was reacted at 35 C until completion (TLC monitoring). Addition of water to the mixture was followed by separation of layers and removal of the organic layer. Evaporation of solvent and column chromatographic separation on silica gel afforded the desired ester as a white solid (5.5 g).

REFERENCES

1. Law M. R., Wald N. J., Wu., Hacksaw Z A., Bailey A.; Systemic underestimation of association between serum cholesterol concentration and ischemic heart disease in observational studies: Data from BUPA Study; *Br. Med. J.* 1994; 308:363-366
2. Law M. R., Wald N. J., Thompson S. G.; By how much and how quickly does reduction in serum cholesterol concentration lower risk of ischemic heart disease? *Br. Med. J.* 1994; 308:367-373
3. La Rosa J. C., Hunninghake D. Bush D. et al.; The cholesterol facts: A summary of the evidence relating to dietary fats, serum cholesterol and coronary heart disease: A joint statement by the American Heart Association and the National Heart, Lung and Blood Institute. *Circulation* 1990; 81:1721-1733
4. Havel R. J., Rapaport E. Drug Therapy: Management of Primary Hyperlipidemia. *New England Journal of Medicine*, 1995; 332:1491-1498
5. Kuccodkar et al.; Effects of plant sterols on cholesterol metabolism. *Atherosclerosis,* 1976; 23:239-248
6. Lees R. S., Lees A. M. Effects of sitosterol therapy on plasma lipid and lipoprotein concentrations. In: Greten H (Ed) Lipoprotein Metabolism. Springer-Verlag, Berlin, Heidelberg, N.Y., 1976:119-124
7. Lees A. M., Mok H. Y. I., Lees R. S., McCluskey M. A., Grundy S. M. Plant sterols as cholesterol-lowering agents: clinical trials in patients with hypercholesterolemia and studies of sterol balance. *Atherosclerosis* 1977; 28: 325-338

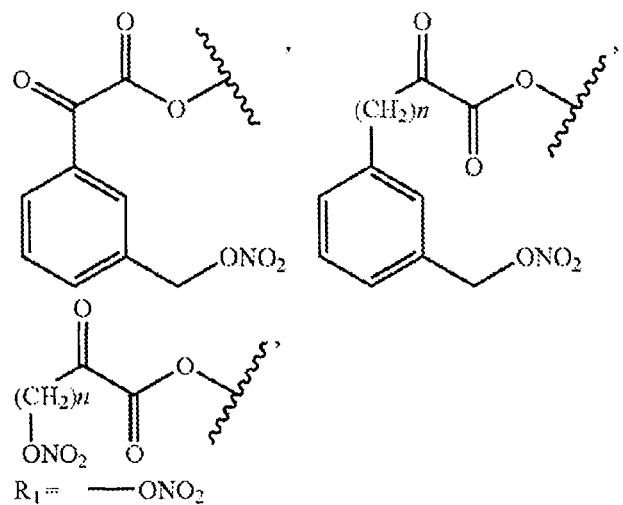

We claim:

1. Sterol and/or stanol nitroderivatives, including pharmaceutically acceptable salts and stereoisomers thereof, represented by the general formulae:

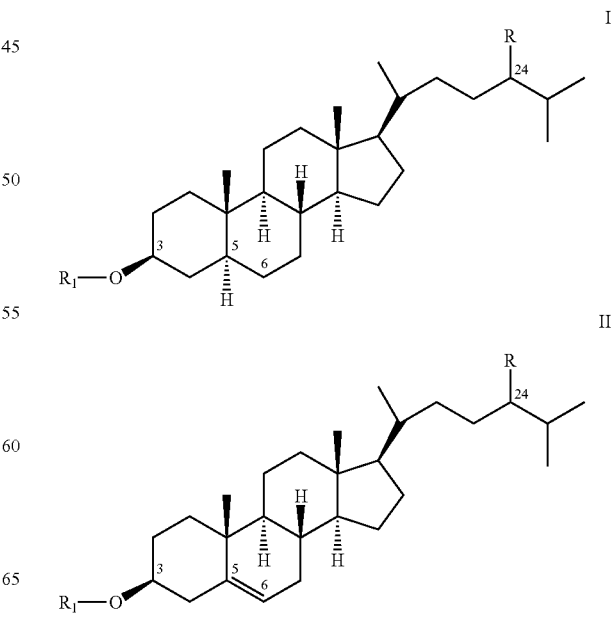

-continued

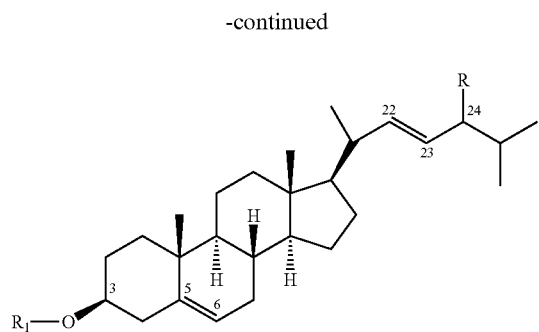

wherein in the foregoing formulae, R is selected from $CH_3$ and $CH_2CH_3$ and $R_1$ is an aromatic or aliphatic NO releasing agent selected from the group consisting of:

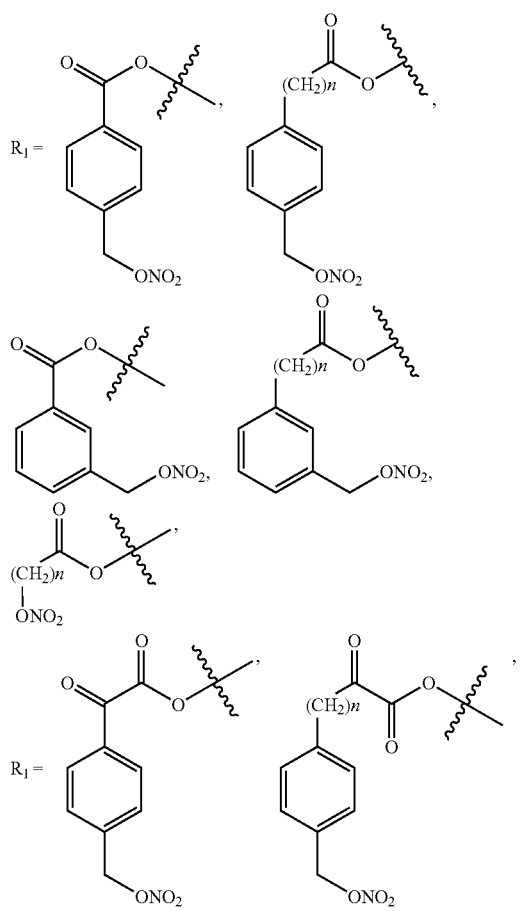

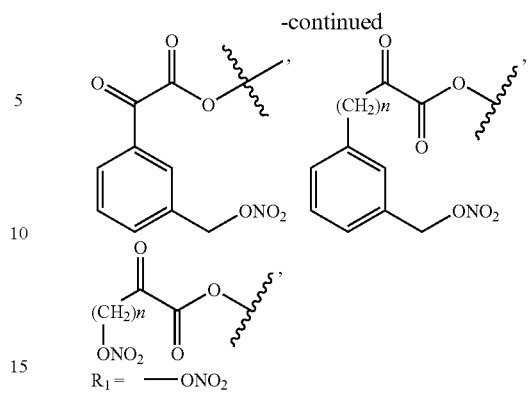

wherein n is an integer from 1 to 20.

2. The nitroderivatives of claim 1 wherein the sterol and stanol are selected from the group consisting of sitosterol, campesterol, stigmasterol, brassicasterol, desmosterol, chalinosterol, poriferasterol, clionasterol, sitostanol, campestanol, stigmastanol, brassicastanol, desmostanol, chalinostanol, poriferastanol, and clionastanol.

3. Pharmaceutical compositions comprising the sterol and/or stanol nitroderivatives of claim 1 and one or more suitable carriers, excipients or adjuvants.

4. The sterol/stanol nitroderivatives of claim 1 wherein the sterol and stanol are in either a natural or synthesized form.

5. The sterol/stanol nitroderivatives of claim 1 wherein the sterol and stanol are in any one of their isomeric forms.

6. The sterol/stanol nitroderivatives of claim 1 wherein the sterol/stanol is selected from the group consisting of sitostanol, sitosterol, campestnaol and campesterol.

7. Pharmaceutical compositions comprising the sterol/stanol nitroderivatives of claim 1 and at least one agent which reduces cholesterol synthesis in humans.

8. The pharmaceutical compositions of claim 7 wherein the agent is a 3-hydroxy-3-methyl glutaryl coenzyme-A (HMG-CoA) reductase inhibitor.

9. Pharmaceutical compositions comprising the sterol/stanol nitroderivatives of claim 1 and one or more of the following: ACE inhibitors, angiotensin II receptor antagonists, beta-andrenergic blockers, calcium channel blockers, and anti-thrombotics.

10. The pharmaceutical compositions of claim 9, wherein the anti-thrombotics are selected from aspirin, nitrosated ACE inhibitors, nitrosated angiotensin II receptor antogonists, nitrosated beta-andrenergic blockers, and nitrosated aspirin.

\* \* \* \* \*

UNITED STATES PATENT AND TRADEMARK OFFICE
CERTIFICATE OF CORRECTION

PATENT NO. : 7,645,749 B2 Page 1 of 1
APPLICATION NO. : 11/396924
DATED : January 12, 2010
INVENTOR(S) : Orchansky et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 624 days.

Signed and Sealed this

Sixteenth Day of November, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,645,749 B2 |
| APPLICATION NO. | : 11/396924 |
| DATED | : January 12, 2010 |
| INVENTOR(S) | : Patricia Liliana Orchansky et al. |

It is certified that error appears in the above-identified patent and that said Letters Patent is hereby corrected as shown below:

IN THE SPECIFICATIONS:

In column 3, lines 5-28, please delete current $R_1$ groups and replace them with the following $R_1$ groups:

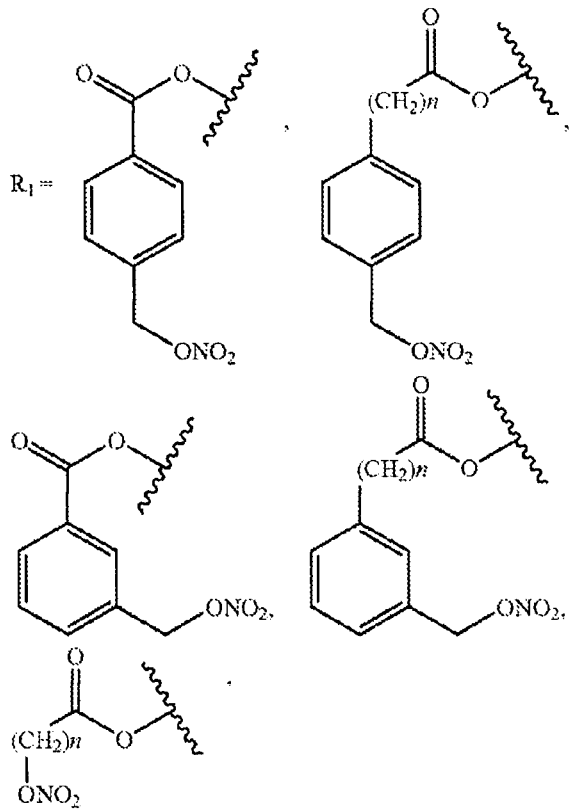

Signed and Sealed this
Twenty-eighth Day of February, 2012

David J. Kappos
*Director of the United States Patent and Trademark Office*

In column 3, lines 29-53, please delete current $R_1$ groups and replace them with the following $R_1$ groups:
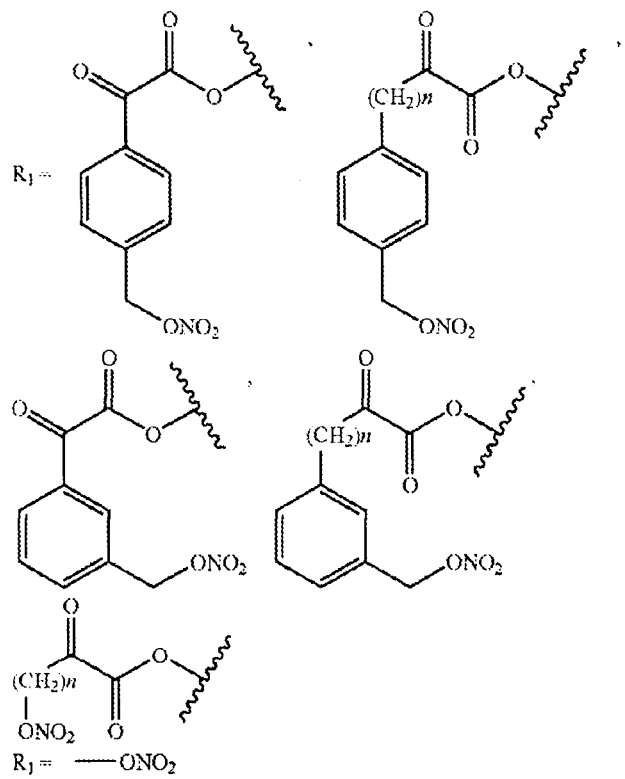
In column 13, lines 20-53, please delete current $R_1$ groups and replace them with the following $R_1$ groups:
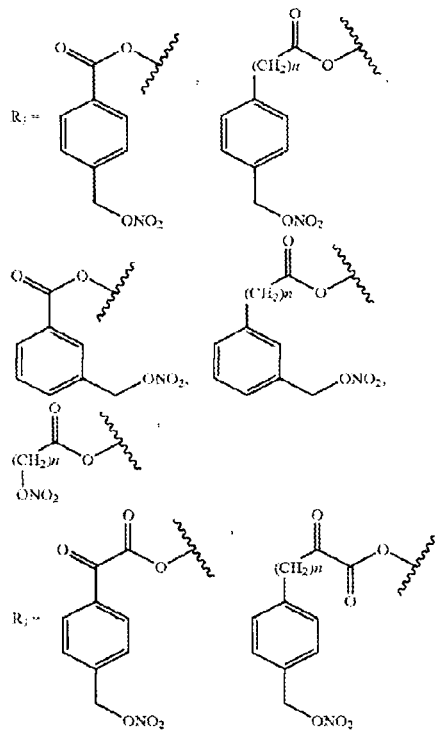

CERTIFICATE OF CORRECTION (continued)

In column 14, lines 1-16, please delete current $R_1$ groups and replace them with the following $R_1$ groups: